United States Patent
Hauptmann

(10) Patent No.: US 12,251,565 B2
(45) Date of Patent: Mar. 18, 2025

(54) DYNAMIC COORDINATED RESET (DCR) STIMULATION

(71) Applicant: nemotec GmbH, Starnberg (DE)

(72) Inventor: Christian Hauptmann, Starnberg (DE)

(73) Assignee: nemotec GmbH, Starnberg (DE)

( * ) Notice: Subject to any disclaimer, the term of this patent is extended or adjusted under 35 U.S.C. 154(b) by 396 days.

(21) Appl. No.: 17/635,005

(22) PCT Filed: Jul. 6, 2020

(86) PCT No.: PCT/EP2020/069010
§ 371 (c)(1),
(2) Date: Feb. 14, 2022

(87) PCT Pub. No.: WO2021/028119
PCT Pub. Date: Feb. 18, 2021

(65) Prior Publication Data
US 2022/0288396 A1 Sep. 15, 2022

(30) Foreign Application Priority Data
Aug. 14, 2019 (DE) .................... 10 2019 005 708.2

(51) Int. Cl.
*A61N 1/00* (2006.01)
*A61N 1/05* (2006.01)
*A61N 1/36* (2006.01)

(52) U.S. Cl.
CPC ....... *A61N 1/36175* (2013.01); *A61N 1/0529* (2013.01); *A61N 1/36139* (2013.01)

(58) Field of Classification Search
None
See application file for complete search history.

(56) References Cited

U.S. PATENT DOCUMENTS

| 7,917,221 B2 | 3/2011 | Tass |
| 8,463,386 B2 | 6/2013 | Tass |

(Continued)

FOREIGN PATENT DOCUMENTS

| DE | 102007003565 A1 | 7/2008 |
| DE | 102014115994 A1 | 5/2016 |

OTHER PUBLICATIONS

Adamchic, Ilya et al; "Coordinated Reset Neuromodulation for Parkinson's Disease: Proof-of-Concept Study"; Movement Disorders; Apr. 21, 2014; pp. 1-6; John Wiley & Sons, Inc.; Hoboken, USA.

(Continued)

*Primary Examiner* — Sana Sahand
(74) *Attorney, Agent, or Firm* — LEYDIG, VOIT & MAYER, LTD.

(57) ABSTRACT

A neurostimulator is configured to activate a set of N electrodes, which are each adapted to stimulate at least a portion of a population of neurons when activated and applied in an invasive manner, at respective onset times $T_1 \ldots T_N$ throughout a cycle period T. N is an integer larger than two and the cycle period T is defined as a time period within which each of the N electrodes is activated exactly once. The onset times $T_1 \ldots T_N$ are not arranged substantially uniformly throughout the cycle period T.

20 Claims, 6 Drawing Sheets

(56) References Cited

U.S. PATENT DOCUMENTS

| | | |
|---|---|---|
| 9,592,384 B2 | 3/2017 | Tass |
| 10,617,869 B2 | 4/2020 | Tass et al. |
| 2012/0010680 A1* | 1/2012 | Wei ................... A61N 1/36062 607/40 |
| 2013/0245713 A1 | 9/2013 | Tass |
| 2015/0018898 A1 | 1/2015 | Tass |
| 2016/0243364 A1 | 8/2016 | Tass et al. |
| 2017/0361105 A1 | 12/2017 | Agnesi et al. |
| 2019/0151657 A1 | 5/2019 | Tyulmankov et al. |

OTHER PUBLICATIONS

Buhlmann, J. et al; "Modeling of a segmented electrode for desynchronizing deep brain stimulation"; Frontiers in Neuroengineering; Dec. 2011; pp. 1-8; vol. 4; Art. 15; Frontiers Media SA; Lausanne, Switzerland.

Deuschl, Guenther et al; "A Randomized Trial of Deep-Brain Stimulation for Parkinson's Disease"; The New England Journal of Medicine; Aug. 31, 2006; pp. 896-908; vol. 355; Massachusetts Medical Society; Waltham, USA.

Hauptmann, C. et al; "External trial deep brain stimulation device for the application of desynchronizing stimulation techniques"; Journal of Neural Engineering; Oct. 16, 2009; pp. 1-12; vol. 6; IOP Publishing Ltd; Bristol, UK.

Hauptmann, Christian et al; "Therapeutic rewiring by means of desynchronizing brain stimulation"; BioSystems; Dec. 2007; pp. 173-181; vol. 89; Elsevier Ireland Ltd; Shannon, Ireland.

Kuehn, Andrea A. et al; "High-Frequency Stimulation of the Subthalamic Nucleus Suppresses Oscillatory β Activity in Patients with Parkinson's Disease in Parallel with Improvement in Motor Performance"; The Journal of Neuroscience; Jun. 11, 2008; pp. 6165-6173; vol. 28; Art. 24; Society for Neuroscience; Washington D.C., USA.

Kuramoto, Yoshiki; "Chemical Oscillations, Waves, and Turbulence"; Springer Series in Synergetics; Dec. 1984; vol. 19; ISBN: 9780486428819; Springer-Verlag; Berlin Heidelberg New York Tokyo; Preface and Table of contents.

Little, Simon et al; "Adaptive Deep Brain Stimulation in Advanced Parkinson Disease"; Annals of Neurology; Apr. 2013; pp. 449-457; vol. 74; No. 3; John Wiley & Sons, Inc .; Hoboken, USA.

Rosin, Boris et al; "Closed-Loop Deep Brain Stimulation Is Superior in Ameliorating Parkinsonism"; Neuron; Oct. 20, 2011; pp. 370-384; vol. 72; Elsevier Inc.; Amsterdam, Netherlands.

Tass, Peter A. et al; "Coordinated Reset Has Sustained Aftereffects in Parkinsonian Monkeys"; Annals of Neurology; Nov. 2012; pp. 816-820; vol. 72; No. 5; John Wiley & Sons, Inc.; Hoboken, USA.

Tass, P. A. et al; "Long-lasting desynchronization in rat hippocampal slice induced by coordinated reset stimulation"; Physical Review; Jul. 2, 2009; pp. 1-4; vol. 80; The American Physical Society; Maryland, USA.

Tass, Peter A.; "A model of desynchronizing deep brain stimulation with a demand-controlled coordinated reset of neural subpopulations"; Biological Cybernetics; Jul. 2003; pp. 81-88; vol. 89; Springer-Verlag; Germany.

Tass, Peter A. et al.; "Long-term anti-kindling effects of desynchronizing brain stimulation: a theoretical study"; Biological Cybernetics; Nov. 12, 2005; pp. 58-66; vol. 94; Springer-Verlag; Germany.

Temperli, P. et al; "How do parkinsonian signs return after discontinuation of subthalamic DBS?"; Neurology; Sep. 7, 2002; pp. 78-81; vol. 60; American Academy of Neurology; Minneapolis, Minnesota, USA.

Wang, Jing et al; "Coordinated Reset Deep Brain Stimulation of Subthalamic Nucleus Produces Long-Lasting, Dose-Dependent Motor Improvements in the 1-Methyl-4-Phenyl-1,2,3,6-Tetrahydropyridine Non-Human Primate Model of Parkinsonism"; Brain Stimulation; Mar. 18, 2016; pp. 1-28; Elsevier; Amsterdam, Netherlands.

\* cited by examiner

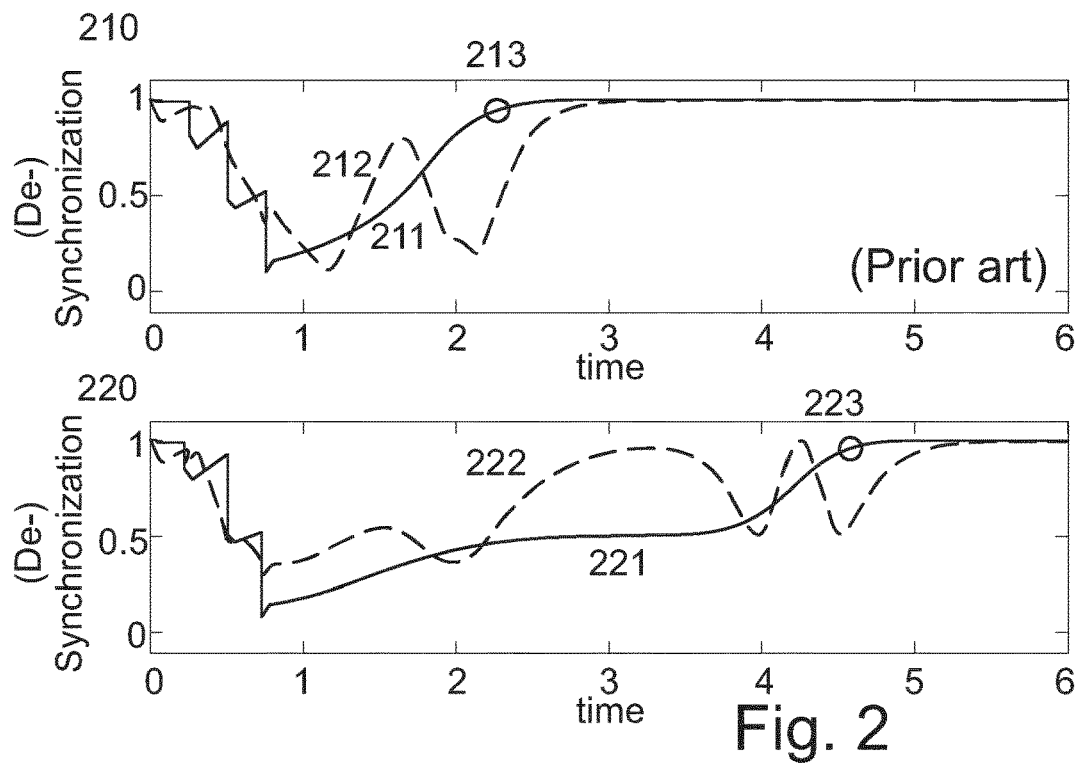
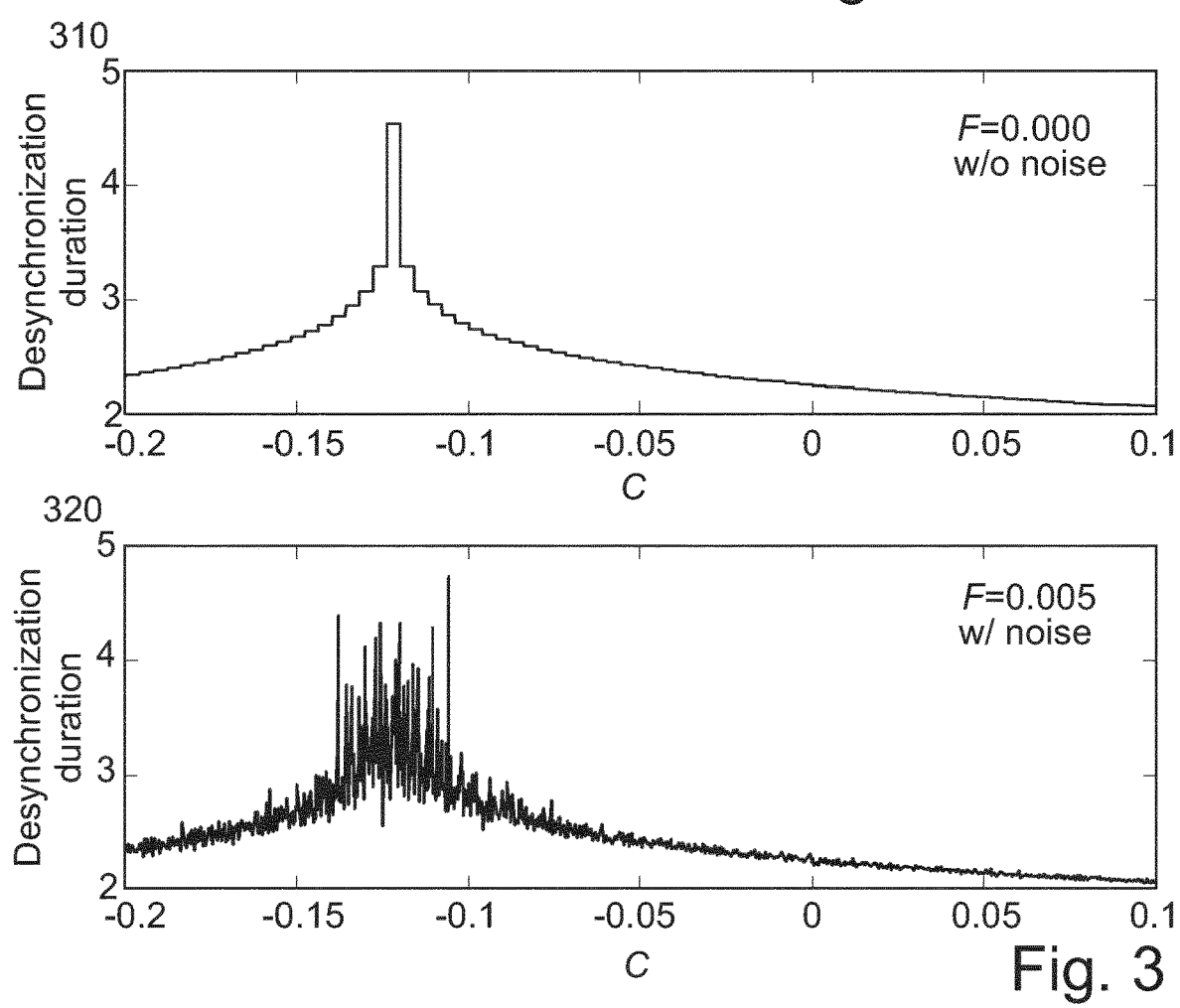
Fig. 2
Fig. 3

DYNAMIC COORDINATED RESET (DCR) STIMULATION

CROSS REFERENCE TO RELATED APPLICATIONS

This application is a U.S. National Phase application under 35 U.S.C. § 371 of International Application No. PCT/EP2020/069010, filed on Jul. 6, 2020, and claims benefit to German Patent Application No. DE 10 2019 005 708.2, filed on Aug. 14, 2019. The International Application was published in English on Feb. 18, 2021 as WO 2021/028119 A1 under PCT Article 21(2).

FIELD

Described and disclosed herein are various systems, devices, components and methods for invasive Dynamic Coordinated Reset (DCR) stimulation. The invention allows to treat, e.g., movement disorders including Parkinson's Disease and/or disabling spasms from strokes, tremor and/or akinesia.

BACKGROUND

Deep brain stimulation (DBS) of the subthalamic nucleus (STN) is an established treatment for patients suffering from advanced Parkinson's disease (PD) (cf. Deuschl et al., N Engl J Med 2006; 355: 896-908). Further stimulation approaches, for instance closed-loop neurostimulation, that have only been tested in an acute setting, showed to be more effective than classical DBS concerning the reduction of motor signs and oscillatory activity in Parkinsonian MPTP-treated primates and PD patients during stimulus delivery (cf. Rosin et al., Neuron 2011, 72: 370-384; Little et al., Ann Neurol 2013, 74: 449-457).

Another novel approach, electrical Coordinated Reset (CR) neuromodulation, specifically targets pathological neuronal synchrony by desynchronization and is based on extensive computational and in-vitro studies (cf. Tass, Biol Cybern 2003, 89: 81-88; Tass & Majtanik, Biol Cybern 2006, 94: 58-66, Hauptmann & Tass, BioSystems 2007, 89: 173-181; Tass et al., Physical Review E 2009, 80, 011902). CR neuromodulation comprises a consecutive, equidistant delivery of brief high-frequency pulse trains through different stimulation contacts or electrodes of an implanted lead. The stimulation achieved thereby intends to sequentially reset phases of different stimulated (sub-)populations of neurons and, hence, divide a population of neurons into phase-shifted sub-populations. The desynchronization induced thereby ultimately causes an unlearning of both pathological neuronal synchrony and pathological synaptic connectivity by utilizing the brain's synaptic plasticity.

According to numerical simulations and clinical studies, CR neuromodulation of sufficient duration may be able to shift a neuronal population into a stable desynchronized state, characterized by reduced symptoms.

Accordingly, it could be expected that neuronal desynchronization along with its positive effects on motor control may outlast the CR neuromodulation duration. After termination of conventional high-frequency stimulation in both MPTP-treated monkeys and PD patients only short-lasting aftereffects were observed, though (cf. Temperli et al., Neurology 2003, 60: 78-81). Additionally, abnormal oscillatory activity, as for example observed in an Electroencephalography (EEG) or local field potentials (LFP), reemerges shortly after turning off classical DBS (cf. Kuhn et al., J Neurosci 2008, 28: 6165-6173). In contrast, CR neuromodulation delivered on 5 consecutive days in MPTP-treated primates had both acute and sustained long-lasting aftereffects on motor function for up to 30 days (cf. Tass et al., Ann Neurol 2012, 72: 816-820; Wang et al., Brain Stimul. 2016 9(4): 609-617). Also in humans suffering from Parkinson's disease, the application of electrical CR neuromodulation delivered for 4 hours per day on 3 consecutive days resulted in lasting beneficial effects on both Parkinson symptoms and hyperactive brain activity as shown by established PD scores and LFP recordings (cf. Adamchic et al., Mov Disord 2014, 29: 1679-1684).

The above-described CR neuromodulation pattern uses a simple and static protocol for application of electrical stimulation pulses as described e.g. in U.S. Pat. Nos. 7,917,221; 13,887,713; 8,463,386 and 9,592,384. In particular, timing of the stimulation pulses is typically chosen to be equidistant. Another example of such an equidistant timing relationship between stimulation pulses may be found in US 2017/361105 which provides systems and methods for combining tonic deep brain stimulation (DBS) and what it calls random DBS. Such a system includes a stimulation lead including a plurality of contacts, and an implantable pulse generator (IPG) communicatively coupled to the stimulation lead and configured to cause tonic stimulation to be delivered using one contact of the plurality of contacts, and cause locally random stimulation to be delivered using a subset of the remaining contacts of the plurality of contacts.

SUMMARY

In an embodiment, the present disclosure provides a neurostimulator configured to activate a set of N electrodes, which are each adapted to stimulate at least a portion of a population of neurons when activated and applied in an invasive manner, at respective onset times $T_1 \ldots T_N$ throughout a cycle period T. N is an integer larger than two and the cycle period T is defined as a time period within which each of the N electrodes is activated exactly once. The onset times $T_1 \ldots T_N$ are not arranged substantially uniformly throughout the cycle period T.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following:

FIG. 2: (De-)synchronization over time as simulated for a stimulation method as known in the prior art (upper panel) and for a stimulation method according to an embodiment of the present disclosure (lower panel);

FIG. 3: Desynchronization duration as simulated for different embodiments of the present disclosure when not taking into account noise (upper panel) as well as when taking into account noise (lower panel);

DETAILED DESCRIPTION

Figure 1A:
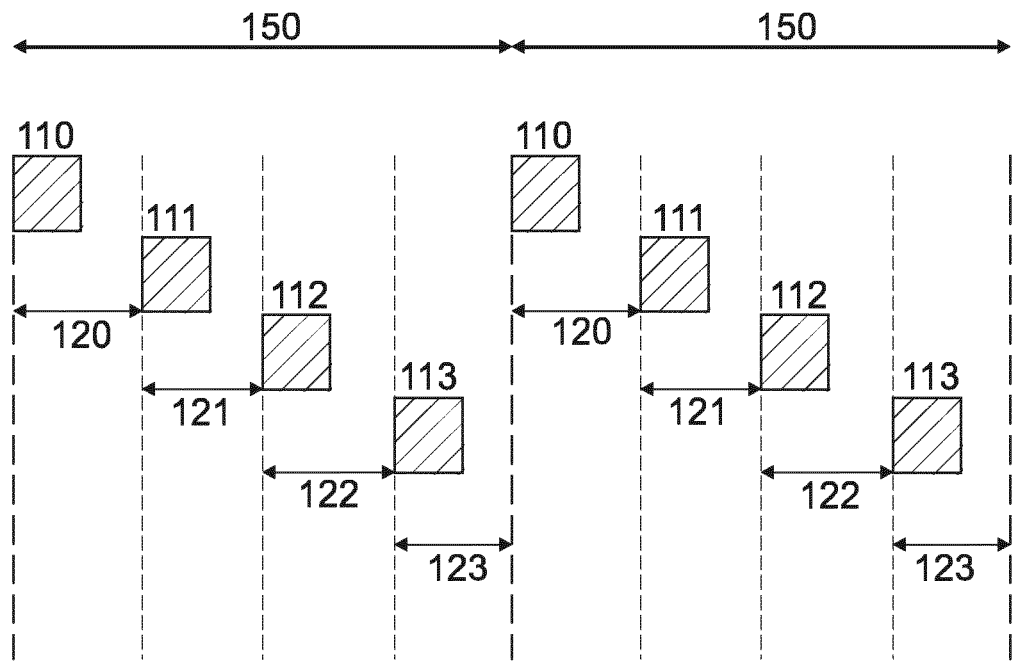
FIG. 1A: Illustration of two consecutive cycle periods as known in the prior art.

Embodiments of the present disclosure provide to further enhance the effects of CR neuromodulation, in particular, to render its effects even stronger and longer lasting.

In an embodiment, a device, which may be a device for desynchronizing neuronal brain activity, comprises means for activating a set of N electrodes at respective onset times $T_1 \ldots T_N$ throughout a cycle period T, wherein N is an integer larger than one. Each electrode is adapted to stimulate at least a portion of a population of neurons when activated and is applied in an invasive manner. In particular, the onset times $T_1 \ldots T_N$ are not arranged substantially uniformly throughout the cycle period T. That is, the onset times $T_1 \ldots T_N$ are especially not arranged in uniform intervals substantially equal to T/N throughout the cycle period T.

Throughout this disclosure, a set of N electrodes is not only meant to define which electrodes are activated, but also in what sequence and/or order they are activated. In other words, a set of N electrodes is an ordered set. That is, a set of N electrodes is not necessarily the same as a set of M electrodes, even if M may be equal to N. To the contrary, while both sets may comprise the same electrodes, the set of N electrodes may comprise and/or define a different activation sequence and/or order than the set of M electrodes. For example, if there are four electrodes A, B, C and D (i.e., N=4), then there may be multiple, different sets of these four electrodes, such as {A, B, C, D}, {B, C, D, A}, {C, D, A, B}, {D, A, B, C}, {B, A, C, D}, {B, A, D, C}, and so forth. In some embodiments, the set of N electrodes, e.g., the sequence in which the N electrodes are to be activated, is selected randomly or pseudo-randomly.

There may be a one-to-one correspondence between electrodes of a set of electrodes and respective onset times. For example, the first electrode of a(n ordered) set of electrodes may be activated at respective onset time $T_1$, the second electrode of the (ordered) set of electrodes may be activated at respective onset time $T_2$, and so forth.

It is also to be noted that, while different electrodes are generally adapted to stimulate different portions of a population of neurons, these portions may nevertheless overlap. That is, a first portion of a population of neurons that may be stimulated by a first electrode and a second portion of said population of neurons that may be stimulated by a second electrode may partly comprise the same neurons. In other words, some neurons may be comprised in the first portion as well as in the second portion. In yet other words, the intersection of the first portion and the second portion does not have to be empty, although it may be in some embodiments.

In some embodiments, the cycle period T may be defined as a (longest) time period within which each of the N electrodes is activated exactly once. The cycle period may also be defined as a duration between two consecutive onset times at which a same electrode of the N electrodes is activated.

Thus, a device may be provided that provides for particularly strong and long-lasting effects, e.g., for treating movement disorders including Parkinson's disease and/or for disabling spasms from strokes, tremor and/or akinesia. Different from the prior art, embodiments of the present disclosure take into account that sub-populations (i.e., portions of the population of neurons) that received stimulation pulses early in a cycle period (e.g. sub-populations mainly affected by first and second pulses of a cycle period) are additionally affected through synaptic connectivity in the course of the further stimulation cycle.

In other words, the device may be configured to activate the set of N electrodes at respective onset times $T_1 \ldots T_N$ based at least in part on a state of at least a portion of the population of neurons. This state may be determined based at least in part on determining one or more electrodes that were activated before in the cycle period and/or based at least in part on determining one or more respective onset times at which one or more electrodes were activated before in the cycle period and/or based at least in part on a refractory period of at least a portion of the population of neurons. That is, the sequence in which electrodes are activated, the onset times at which they are activated as well as the refractory period are interrelated. For example, the position of a given electrode in an activation sequence as well as the respective onset time at which it accordingly is to be activated may depend on which electrode was or which electrodes were activated at which onset time or onset times before in the cycle period.

Hence, by taking into account synaptic connectivity, the dynamic—rather than static—timing configuration of CR stimulation pulses which embodiments of the present disclosure provide for may result in significantly stronger and longer-lasting desynchronization within a population of neurons, which may have a stronger and longer-lasting effect on symptoms resulting from Parkinson's disease and the like.

It is to be understood throughout this disclosure that a stimulation pulse is generated by activating a corresponding electrode.

In some embodiments, the device may comprise the set of N electrodes. This may allow to finetune the activation of electrodes, as the device and its operation may hence be adjusted with respect to the specific characteristics of the electrodes used. In effect, this may result in a more precise delivery of stimulation pulses, potentially increasing effectiveness of stimulation.

An onset time $T_i$ of the onset times $T_1 \ldots T_N$ at which an i-th electrode of the N electrodes is activated in the cycle period T may be substantially determined by a function that is nonlinear with respect to i. Relying on a function allows to determine onset times systematically as opposed to, e.g., randomly, thereby enhancing reproducibility. This increased reproducibility may in turn render the stimulation more reliable and possibly also more effective. At the same time, by choosing the function to be non-linear with respect to i, it is ensured that—different than in the prior art—synaptic connectivity is taken into account as described above.

Specifically, in an embodiment, an onset time $T_i$ of the onset times $T_1 \ldots T_N$ at which an i-th electrode of the N electrodes is activated in the cycle period T may be substantially given by $T_i = T/N \cdot (i-1) + T/2N \cdot (1+(-1)^i) \cdot C$, wherein $-1 < C < 0$, preferably $-0.5 \leq C < 0$, most preferably $-0.2 \leq C < 0$.

In another embodiment, an onset time $T_i$ of the onset times $T_1 \ldots T_N$ at which an i-th electrode of the N electrodes is activated in the cycle period T may be substantially given by $T_i = T/N \cdot (i-1) + T/2N \cdot (1+(-1)^i) \cdot C$, wherein $0 < C < 1$, preferably $0 < C \leq 0.5$, most preferably $0 < C \leq 0.2$.

Also, an onset time $T_i$ of the onset times $T_1 \ldots T_N$ at which an i-th electrode of the N electrodes is activated in the cycle period T may be substantially given by $T_i=T/N\cdot(i-1)\cdot C$, wherein $0<C<1$, preferably $0.75\leq C<1$, most preferably $0.5\leq C<1$.

In another embodiment, an onset time $T_i$ of the onset times $T_1 \ldots T_N$ at which an i-th electrode of the N electrodes is activated in the cycle period T may be substantially given by $T_i=T/N\cdot(i-1)\cdot C$, wherein $1<C<N/N-1$.

In yet another embodiment, an onset time T, of the onset times $T_1 \ldots T_N$ at which an i-th electrode of the N electrodes is activated in the cycle period T may be substantially given by $T_i=T/N\cdot(i-1)+T\cdot C$, wherein $C=0$ for $i=1$ and $-1/N<C<0$ for $i>1$.

An onset time $T_i$ of the onset times $T_1 \ldots T_N$ at which an i-th electrode of the N electrodes is activated in the cycle period T may also be substantially given by $T_i=T/N\cdot(i-1)+T\cdot C$, wherein $0<C<1/N$.

In a further embodiment, an onset time $T_i$ of the onset times $T_1 \ldots T_N$ at which an i-th electrode of the N electrodes is activated in the cycle period T may be substantially given by $T_i=T/N\cdot(i-1)+T\cdot(N+1-i)\cdot C$, wherein $C=0$ for $i=1$ and $-1/N\cdot(N-1)<C<0$ for $i>1$.

It is also possible that an onset time $T_i$ of the onset times $T_1 \ldots T_N$ at which an i-th electrode of the N electrodes is activated in the cycle period T may be substantially given by $T_i=T/N\cdot(i-1)+T\cdot(N+1-i)\cdot C$, wherein $0<C<1/N$.

In an embodiment, an onset time $T_i$ of the onset times $T_1 \ldots T_N$ at which an i-th electrode of the N electrodes is activated in the cycle period T may be substantially given by $T_1=0$ for $i=1$ and by $T_i=T_{i-1}+T/N\cdot C^{N+1-i}$ for $i>1$, wherein $0<C<1$, preferably $0.75<C<1$, most preferably $0.5<C<1$.

Alternatively, an onset time $T_i$ of the onset times $T_1 \ldots T_N$ at which an i-th electrode of the N electrodes is activated in the cycle period T may be substantially given by $T_1=0$ for $i=1$ and by $T_i=T_{i-1}+T/N\cdot C^{N+1-i}$ for $i>1$, wherein $1<C$ and $C^N-C/C-1<N$.

Onset times substantially given by any of the above functions have been found to result in particularly effective stimulation, yielding especially strong and long-lasting effects.

When employing any of the above formulas, the device may be configured to determine C based at least in part on an intensity of symptoms resulting from synchronized neuronal brain activity. This may allow finetuning the respective formula, in turn optimizing stimulation which may result in stronger and longer-lasting effects.

If the intensity of the symptoms is determined based at least in part on one or more measurements of neuronal brain activity, C may be determined to a particularly high degree of precision as one immediately measures the quantity at the root for the symptoms.

In some embodiments, the symptoms may comprise a tremor. Then, the intensity of the symptoms may be determined based at least in part on one or more measurements of the tremor, preferably using a movement sensor and/or an accelerometer. This in effect allows for a particularly easy and user-friendly determination of the intensity of the symptoms.

In some embodiments, the device may be configured to determine C by carrying out stimulations using values of C that lie around an initial value of C determined based at least in part on the intensity of the symptoms. That is, rather than employing the value of C determined based at least in part on the intensity of the symptoms indefinitely, the device may also use this value of C, e.g., as a starting point for an iterative sequence of stimulations that may yield an optimized value for C different from that determined based at least in part on the intensity of the symptoms. This may further optimize stimulation, resulting in stronger and longer-lasting effects.

The device may be configured to randomly or pseudo-randomly select the set of N electrodes within a plurality of electrodes. That is, there may be more than N electrodes the device may activate. This may allow to stimulate a larger number of different portions of a population of neurons without rearranging and/or reapplying any of the electrodes. First of all, this is desirable because the electrodes are applied in an invasive manner, such that rearranging and/or reapplying them is not only complex and expensive, but also hazardous. Irrespective thereof, rearranging and/or reapplying electrodes could in principle induce slight variations and/or changes in the device's behavior. Possibly, even failure could ensue due to mechanical stress exerted during rearrangement and/or reapplication. By avoiding such variations and/or changes, stimulation may be rendered more reliable and also predictable.

Moreover, randomly or pseudo-randomly selecting the set of N electrodes within a plurality of electrodes may be of particular use where different sets of electrodes are to be activated throughout different cycle periods of a plurality of consecutive cycle periods as will be described in greater detail below. Due to random or pseudo-random selection, a reasonable degree of certainty may be attained that each portion of the population of neurons is stimulated approximately evenly, e.g., an approximate same number of times.

The N electrodes may be activated for a respective activation time each at the respective onset time. Then, the activation times may overlap in time at most partly, preferably by at most 50%, more preferably by at most 20%, even more preferably by at most 10%, and most preferably not at all. Minimizing an overlap between activation times may render stimulation more predictable and reliable because it reduces the risk of inducing a coupling and/or resonance between different portions of the population of neurons that are stimulated by the respective electrodes. In effect, this adds to the key goal of embodiments of the present disclosure to achieve neuronal desynchronization.

The device may furthermore be configured to activate the set of N electrodes throughout at least two and at most 100 consecutive cycle periods. Repeat stimulation has been found to yield stronger and longer-lasting effects.

When repeatedly stimulating, the device may be configured to activate the set of N electrodes at respective onset times $T_1 \ldots T_N$ throughout at least one of the at least two and at most 100 cycle periods based at least in part on a state of the population of neurons. That is, for choosing the onset times, the device may take into account the state of the population of neurons, eventually using onset times that are set to yield the best results. The state of the population of neurons may be determined based at least in part on determining at least one set of electrodes that was activated in one or more preceding cycle periods and/or based at least in part on determining respective onset times at which a set of electrodes was activated in one or more preceding cycle periods and/or based on a refractory period of at least a portion of the population of neurons. In other words, the device may for instance take into account which electrodes were activated at which onset times in one or more preceding cycle periods. In effect, all these measures may optimize repeat stimulation and may therefore yield stronger and longer-lasting effects.

In some embodiments, the device may be configured to activate the set of N electrodes at different respective onset times $T_1 \ldots T_N$ throughout the at least two and at most 100 cycle periods. That is, the respective onset times $T_1 \ldots T_N$ for a first cycle period of the at least two and at most 100 cycle periods may be different from the respective onset times $T_1 \ldots T_N$ for a second cycle period of the at least two and at most 100 cycle periods. In other words, the respective onset times $T_1 \ldots T_N$ may vary across the at least two and at most 100 cycle periods. For example, the respective onset times $T_1 \ldots T_N$ for the first cycle period may be substantially given by a different formula than the respective onset times $T_1 \ldots T_N$ for the second cycle period. That is, the respective onset times $T_1 \ldots T_N$ for the first cycle period may for example be substantially given by a first of the above-disclosed formulas, and the respective onset times $T_1 \ldots T_N$ for the second cycle period may be substantially given by a second of the above-disclosed formulas different from the first.

In some embodiments, the respective onset times $T_1 \ldots T_N$ may vary across the at least two and at most 100 cycle periods because, for each cycle period of the at least two and at most 100 cycle periods, the respective onset times $T_1 \ldots T_N$ are based at least in part on a state of the population of neurons: As the state of the population of neurons may change over the course of the at least two and at most 100 cycle periods due to stimulation, the respective onset times $T_1 \ldots T_N$ may vary across the at least two and at most 100 cycle periods, too. Such dynamic choice of the respective onset times $T_1 \ldots T_N$ may optimize repeat stimulation and therefore yield stronger and longer-lasting effects.

In other embodiments, the device may be configured to activate the set of N electrodes at the same respective onset times $T_1 \ldots T_N$ throughout the at least two and at most 100 cycle periods. This may yield particularly predicable and/or reproducible results and may also decrease computational complexity.

In addition to or as an alternative to varying the respective onset times $T_1 \ldots T_N$ across at least two and at most 100 cycle periods as just described, the device may also vary the (sets of) electrodes that are being activated across the at least two and at most 100 cycle periods. That is, the device may be configured to activate a further set of M electrodes different from the set of N electrodes throughout at least two and at most 100 cycle periods, wherein M is an integer. M may be smaller than, equal to, or larger than N. It is reiterated that, throughout this disclosure, a set of N electrodes does not only define which electrodes are activated, but also in what sequence and/or order. That is, even though M may be equal to N, this does not imply that the set of M electrodes is the same as the set of N electrodes. To the contrary, both sets may comprise the same electrodes, but at the same time define a different activation sequence and/or order of these electrodes.

The device may vary the (sets of) electrodes that are being activated across the at least two and at most 100 cycle periods because it is configured to activate the further set of M electrodes based at least in part on a state of the population of neurons. However, in some embodiments, activating (sets of) electrodes based at least in part on a state of the population of neurons may result in the same set of N electrodes being activated over at least two of the at least two and at most 100 cycle periods. As already mentioned above, the device may be configured to determine the state of the population of neurons based at least in part on determining at least one set of electrodes that was activated in one or more preceding cycle periods and/or based at least in part on determining respective onset times at which a set of electrodes was activated in one or more preceding cycle periods and/or based on a refractory period of at least a portion of the population of neurons. In effect, all these measures may optimize repeat stimulation and may therefore yield stronger and longer-lasting effects.

The device may further be configured not to activate any electrodes for a duration corresponding to at least one cycle period and at most 100 cycle periods in alternation with activating electrodes throughout at least one and at most 100 consecutive cycle periods. For example, there may be 3 cycle periods of stimulation followed by a stimulation break of a duration corresponding to 2 cycle periods, followed by 3 cycle periods of stimulation followed by a stimulation break of a duration corresponding to 2 cycle periods, and so forth. Providing such stimulation breaks may avoid overstimulation, which may in turn enhance stimulation effects, rendering them stronger and longer lasting.

Longer and/or more complex stimulation patterns may also be possible. For example, there may be 3000 cycle periods of stimulation followed by a stimulation break of a duration corresponding to 150 cycle periods. For a cycle period of 200 milliseconds, this results in 10 minutes of stimulation followed by a 30 second stimulation break. In some embodiments, instead of providing stimulation for 10 minutes straight, there may also be a (sub-)pattern in place. That is, stimulation may be provided in the form of a repeat pattern, e.g., comprising 3 cycle periods of stimulation followed by a (shorter) stimulation break of a duration corresponding to 2 cycle periods. After following this pattern for a duration corresponding to, e.g., 3000 cycle periods, there may then be a longer stimulation break of a duration corresponding to, e.g., 150 cycle periods.

In light of the above, the skilled person will appreciate that embodiments of the present disclosure allow to vary which electrodes—if any—are activated at which onset times across a plurality of consecutive cycle periods at will, as long as there is no cycle period throughout which the respective onset times $T_1 \ldots T_N$ are arranged substantially uniformly. As stated above, in effect, such variation(s) may optimize repeat stimulation and may therefore yield stronger and longer-lasting effects.

In another aspect, a method is provided which may be a method for desynchronizing neuronal brain activity. The method comprises activating a set of N electrodes at respective onset times $T_1 \ldots T_N$ throughout a cycle period T As above, N is an integer larger than one. Each electrode is adapted to stimulate at least a portion of a population of neurons when activated and is applied in an invasive manner. In particular, the onset times $T_1 \ldots T_N$ are not arranged substantially uniformly throughout the cycle period T. That is, the onset times $T_1 \ldots T_N$ are especially not arranged in uniform intervals substantially equal to T/N throughout the cycle period T. Such method may yield particularly strong and long-lasting stimulation effects.

In yet another aspect, a computer program is provided that comprises instructions which, when the program is executed by a computer, cause the computer to carry out a method as just described.

For the sake of brevity only a few embodiments will be described in the following. The skilled person will recognize that the specific features described with reference to these embodiments may be modified and combined differently and that individual features may also be omitted if they are not essential. The general explanations in the sections above will also be valid for the following more detailed explanations.

Described herein are various systems, devices, components and methods relating to neuromodulation therapies delivered to patients using electrical stimulation techniques and devices.

Typically, a stimulation device may apply stimulation to a confined target area. A target area typically has a size of 1 cm³, but may as well be smaller or larger, for example depending on the size of an affected and/or diseased brain area and/or a used stimulation electrode configuration. Such small brain areas are typically characterized by interconnections between neurons of the target area, either by direct connections or by indirect connections. It is reported in scientific literature that in many diseases strong interaction might cause the neurons to get active in an unusual synchronized manner, called hyper-synchronicity and/or hyper-activity. Such hyper-active and/or hyper-synchronous activity is seen as the cause for symptoms associated with such diseases.

Therefore, it must be assumed that strong interactions between neurons affect the activity of the neurons on any time scale, in particular on timescales of milliseconds and seconds.

A static coordinated reset pattern (as disclosed, e.g., in U.S. Pat. Nos. 7,917,221; 13,887,713; 8,463,386 and 9,592,384) uses a basically equidistant timing of stimulation pulses for direct stimulation of the target area, which is typically supposed to affect different sub-populations of neurons. This does not take into account that in the course of the stimulation cycle (which is to be understood as synonymous with a cycle period throughout this disclosure), which typically has a duration of 10 to 1000 milliseconds, the already stimulated sub-populations, i.e., e.g., the sub-populations stimulated first and second in a stimulation cycle, are affected due to neuronal connectivity also later in the stimulation cycle. Since the goal is to achieve an equally distributed multi-cluster state at the end of each stimulation cycle, a static, equidistant approach cannot yield optimal results. However, as the inventor realized, a dynamic configuration of stimulation timing can improve the performance of desynchronizing stimulation drastically.

Dynamic Coordinated Reset Approach

Figure 1B:
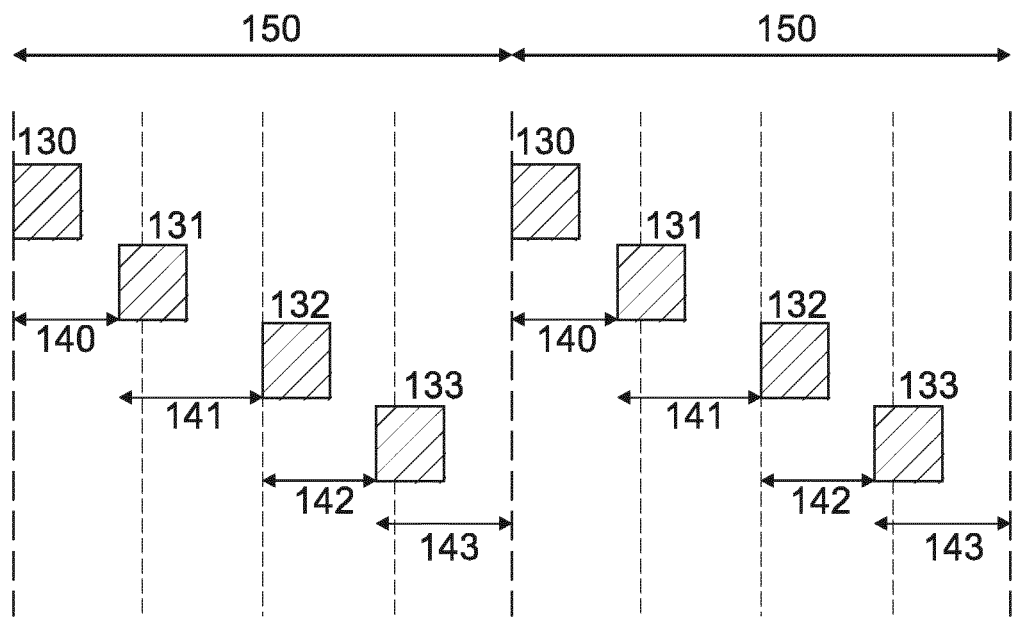
FIG. 1B: Illustration of two consecutive cycle periods according to an embodiment of the present disclosure.

One example of such a dynamic timing configuration is given in FIG. 1B which may best be understood when compared to an example of a static configuration known from the prior art as given in FIG. 1A. In both FIG. 1A and FIG. 1B, two typical stimulation cycles 150 are shown. A length of cycle 150 may be defined by the inverse of a frequency of pathologic activity found in a target structure. In the static CR stimulation approach (as disclosed, e.g., in U.S. Pat. Nos. 7,917,221; 13,887,713; 8,463,386; 9,592,384) shown in FIG. 1A pulses 110-113 may typically comprise an equidistant timing and therefore fill the whole cycle completely. It is noted that the onset time of such a stimulation pulse may be understood to correspond to an onset time at which an electrode is activated and that a duration of such a stimulation pulse may be understood to correspond to an activation time of an electrode. Hence, gaps 120, 121 and 122 have a same length and a gap 123 until a next cycle 150 starts has the same length, as well. Pulses 110-113 may for instance consist of single charge-balanced pulses, or a burst of charge-balanced pulses.

In contrast, the dynamic CR stimulation approach uses a different timing. For example, stimulation pulses such as stimulation pulses 130-133 of FIG. 1B may have a timing characterized by gaps 140-142 of different lengths as shown in FIG. 1B. Preferably, gaps 140 and 142 may have a slightly shorter duration as compared to gaps 120-122 of FIG. 1A. And therefore, a gap 143 until the next cycle starts may be longer than gaps 140 and 142. But depending on a particular neuronal situation, e.g., a state of the population of neurons, it may also be preferred to have shorter gaps at the beginning of cycle 150 and longer gaps at the end, or to have short gaps at the beginning and end of cycle 150 and a prolonged middle gap, or prolonged gaps at the beginning and end of the cycle and a shortened middle gap.

In a general formulation, for standard CR stimulation as known in the prior art, onset times of stimulation pulses $T_i$ may be defined as $$T_i = T/N \cdot (i-1) \tag{1}$$

where i is the index of the i-th stimulation contact (which may be understood to be synonymous with an electrode throughout this disclosures) and hence an integer, T corresponds to the duration of a cycle and could represent typical durations of a cycle like 10 milliseconds or 100 milliseconds or 1000 milliseconds. N is the number of active stimulation contacts and hence also an integer. It is noted that the equations and/or formulas discussed in the following all rely on the same definitions of $T_i$, T, N and i.

In one embodiment of the present disclosure, the timing of the onset of the pulses, and thereby—implicitly—the duration of the gaps could be described by the following exemplary equation (which is to be understood to be synonymous with formula throughout this disclosure) for the onset time of pulse i:

$$T_i = T/N \cdot (i-1) + T/2N \cdot (1 + (-1)^i) \cdot C \tag{2}$$

where T=1, i.e., a duration of the cycle is normalized to 1.0, i.e., 1.0 corresponds to the duration of one cycle and may represent typical durations of a cycle like 10 milliseconds or 100 milliseconds or 1000 milliseconds. Dynamic factor C could be chosen from [−0.2, 0.0 [(i.e., shortened first and third gaps) or chosen from]0.0, 0.2] (i.e., prolonged first and third gaps). More generally, −1<C<0, preferably −0.5≤C<0, most preferably −0.2≤C<0 and/or 0<C<1, preferably 0<C≤0.5, most preferably 0<C≤0.2. Other ranges and formulations are possible, as well.

Shortened gaps, i.e., C from [−0.2, 0.0[, may be a preferable choice, since shortened gaps obey the concept that neuronal connectivity attracts sub-populations stimulated early in the cycle back to the synchronized state and hence subsequent stimuli have to follow faster than proposed by the static CR approach (corresponding to C=0) known from the prior art to compensate for this. If for example C=−0.1 instead of 0.25, first and third gaps 140, 142 would comprise a length of 0.25+C·0.25=0.225. Second and fourth gaps 141, 143 would comprise a length of 0.275.

In an alternative embodiment, onset times $T_1 \ldots T_N$ of pulses could also be described by the following exemplary equation (using a normalized duration of a cycle as before), for the onset time of pulse i:

$$T_i = T/N \cdot (i-1) \cdot C \tag{3}$$

where T is the cycle period, N the number of active contacts in each cycle and i is the index of the start time of the i-th stimulation. Dynamic factor C could be chosen from [0.5, 1.0[(i.e., shortened gaps) or chosen from]1.0, 1.5] (i.e., prolonged gaps). More generally, 0<C<1, preferably 0.75≤C<1, most preferably 0.5≤C<1 and/or 1<C<N/N−1. Other ranges and formulations might be possible, as well.

Notably, the boundaries of the intervals for C are restricted by the duration of the stimulation pulses (e.g., their respective activation times), since it would be favorable to realize a pattern without overlap of pulses.

An alternative embodiment could include a different modification of the onset times of the pulses (using a normalized duration of a cycle as before), e.g.:

$$T_i = T/N \cdot (i-1) \cdot (N+1-i) \cdot C \tag{4}$$

where T is the cycle period, N the number of active contacts in the cycle and i is the index of the stimulation site (which may be understood to be synonymous with an electrode). Dynamic factor C may be chosen from [0.5, 1.0 [(i.e., shortened later gaps) or chosen from]1.0,1.5] (i.e., prolonged gaps). More generally, C<4/N.

Another embodiment could include an absolute rather than relative modification of the onset times of the pulses (using a normalized duration of a cycle as before), e.g.:

$$T_i = T/N \cdot (i-1) + T \cdot (N+1-i) \cdot C \quad (5)$$

where T is the cycle period, N the number of active contacts in each cycle and i is the index of the stimulation site (i.e., electrode) and dynamic factor C could be chosen from [−0.1, 0.0[(i.e., shortened gaps) or chosen from]0.0, 0.1] (i.e., prolonged gaps). More generally, C=0 for i=1 and −1/N·(N−1)<C<0 for i>1 and/or 0<C<1/N. Other ranges and formulations might be possible, as well.

An alternative embodiment could include another absolute rather than relative modification of the starting time of the pulses (using a normalized duration of a cycle as before), e.g.:

$$T_1 = 0 \text{ and } T_i = T_{i-1} + T/N \cdot C^{N+1-i} \text{ for } i>1 \quad (6)$$

where T is the cycle period, N the number of active contacts in the cycle, and i is the index of the stimulation site (i.e., electrode). Dynamic factor C could be chosen from [0.5, 1.0[(i.e., shortened gaps) or chosen from]1.0, 1.5] (i.e., prolonged gaps). More generally, 0<C<1, preferably 0.75<C<1, most preferably 0.5<C<1 and/or 1<C and $C^N$−C/C−1<N. Other ranges and formulations might be possible, as well.

Compared to equation (1), equation (6) results in gaps of different lengths within a cycle. Namely, for N=4 a gap between the first and second pulse is different from a gap between the second and third pulse.

Numerical Model of Neuronal Activity

The effects of the dynamic CR stimulation approach may be exemplified using numerical simulations of neuronal activity in validated models established in scientific literature (e.g., see Tass, Biol Cybern 2003, 89: 81-88; Tass & Majtanik, Biol Cybern 2006, 94: 58-66). We herein use the same system to describe neuronal activity as used by Tass (in Biol Cybern 2003, 89: 81-88; equation 1 therein), which is the so-called phase oscillator model or Kuramoto model (cf. Kuramoto, Chemical oscillations, waves, and turbulence. (1984) Springer, Berlin Heidelberg New York).

The phase of each neuron of a network may be described by a differential equation of the form:

$$\dot{\psi}_j = \Omega - \frac{K}{N} \sum_{k=1}^{N} \sin(\psi_j - \psi_k) + X_j(t) S_j(\psi_j) + F_j(t) \quad (7)$$

where $\psi_j$ denotes the phase of the j-th phase oscillator. All oscillators have the same eigenfrequency $\Omega$ and are globally coupled with strength K/N>0. Noise $F_j(t)$ is Gaussian white noise with $\langle F_j(t) \rangle = 0$ and $\langle F_j(t) F_k(t') \rangle = F \delta_{jk} \delta(t-t')$, where F is a constant noise amplitude. Stimulation impact $X_j(t) S_j(\psi_j)$ was slightly simplified by setting the corresponding neurons to zero in response to stimulation.

The model proposed by Tass (in Biol Cybern 2003, 89: 81-88) was used to develop the static CR approach and was also used as a tool to describe the static CR neuromodulation pattern known in the prior art (cf. U.S. Pat. Nos. 7,917,221; 13,887,713; 8,463,386; 9,592,384). The results of the model were validated by building a device capable of applying static CR neuromodulation (cf. Hauptmann et al., 2009 J Neural Eng. 2009 December; 6(6):066003) and subsequently in several clinical trials using invasive stimulation in animal models (cf. Tass et al., 2012 Ann Neurol. 2012 72(5):816-20; Wang et al., 2016 Brain Stimulation 9(4): 609-617) and human clinical trials (cf. Adamchic et al., 2014 Mov Disord. 2014 November; 29(13):1679-84).

Therefore, it was shown that the numerical model (7) is a valid and reliable numerical model.

Prolonged Period of Desynchronization by Dynamic CR

The validated numerical model (7) was used to study the effects of the dynamic CR approach. For the simulations a phase oscillator network was used where the number of simulated neurons equaled n=100 (not to be confused with the number of electrodes N). Exemplary results for both the static and dynamic CR approach are shown in upper panel 210 and lower panel 220, respectively, of FIG. 2. For the simulations a phase oscillator network was used with n=100 simulated neurons and four stimulation contacts (electrodes), i.e., N=4. Stimulation impact was slightly simplified by setting the corresponding neurons to zero in response to stimulation. This was done to further generalize the model by implementing a simple but effective resetting pulse.

An initially synchronized population (which may correspond to a realistic situation in case of a disease with severe symptoms) is stimulated by one static CR stimulation cycle (cf. upper panel 210) in a first time unit. In the upper panel 210 of FIG. 2, for the static CR approach (equation (1) above or equation (2) above with C=0), a first order parameter 211 (solid line) and a fourth order parameter 212 (dashed line) is shown.

First order parameter 211 is calculated from the phases of the sub-populations or the phases of the neurons within the sub-population using the equation:

$$R_1(t) = \text{abs}\left(\frac{1}{n}\sum_{k=1}^{n} e^{i\psi_k(t)}\right) \quad (8)$$

First order parameter 211 may indicate an extent of synchronization in the network. First order parameter 211 may range from 0 to 1, where 0 indicates a fully desynchronized system and 1 indicates a fully synchronized system (with respect to first order parameter 211).

Fourth order parameter 212 is also calculated from the phases of the sub-populations or the phases of the neurons within the sub-population, however using the equation:

$$R_4(t) = \text{abs}\left(\frac{1}{n}\sum_{1}^{n} e^{i 4 \psi_k(t)}\right) \quad (9)$$

Fourth order parameter 212 is indicating an extent of a four-cluster state in the network. Fourth order parameter 212 also ranges from 0 to 1, where 0 indicates no four-cluster state in the system and 1 indicates a fully expressed four-cluster state.

In the simulations of FIG. 2, connectivity was $$\frac{K}{N} = 0.032,$$

no noise was applied (cf. below for details on the influence of noise) and a stimulation length (i.e., activation time) of 0.2/N was chosen. First order parameter 211 (cf. equation (8) above) is given by the solid black line and fourth order parameter 212 (cf. equation (9) above) is given by the dashed black line. $R_1(t)$, i.e., first order parameter 211, crosses the threshold of 0.95 at t=2.2 (black circle 213), namely, 1.2 time units after the end of a stimulation cycle.

For the dynamic CR approach, using C=−0.122 (cf. equations (1)-(4) above), results as presented in lower panel 220 are observed. One cycle of dynamic CR stimulation is applied. Same parameters are used as in the simulation of upper panel 210. The initially synchronized population is stimulated by one stimulation cycle in a first time unit.

Panel 220 quantifies this observation using a first order parameter 221 (cf. equation (8) above) and a fourth order parameter 222 (cf. equation (9) above), which are indicated by a solid and dashed line, respectively. A long period of desynchronized neuronal activity is achieved by dynamic CR stimulation, namely first order parameter 221 crosses the threshold of 0.95 at time 4.5 (black circle 223), namely, 3.5 time units after the end of a stimulation cycle.

In a direct comparison of the two simulations, it is clear that embodiments of the present disclosure (i.e., dynamic CR stimulation) have the potential to increase the duration of a desynchronized phase by a factor of 2.0 (i.e., comparing respective desynchronization durations of 2.2 and 4.5). Concerning the more relevant duration starting from the end of the stimulation cycle, the improvement factor is even higher, namely 2.8 (i.e., comparing respective desynchronization durations of 2.2-1=1.2 and 4.5-1=3,5).

Influence of Noise

Biological systems generally show noisy behavior; therefore, it is important to test if the observed improvements (cf. above and FIG. 2) are stable when noise is added. Exemplarily, simulations were performed for N=4 whose results are shown in FIG. 3. In a first simulation, no noise was added (F=0.000, n=100, cf. panel 310) and in a second simulation, noise was added (F=0.005, n=100, cf. panel 320). For all simulations, the same parameters were used as used in the simulations for FIG. 2. Namely, connectivity was kept constant at $$\frac{K}{N} = 0.032.$$

A length of the stimulation pulses (i.e., an activation time) was chosen as 0.2/N to allow longer stimulation pulses for lower numbers of contacts/electrodes and shorter stimulation pulses for higher numbers of contacts/electrodes with the goal to avoid an overlap of stimulation pulses and give space for the adaptation of dynamic factor C.

A clear peak structure may be observed in FIG. 3. Actually, in both simulations, a peak is observed for a very similar value of C, i.e., C=−0.122 for no noise and C=−0.106 for added noise. A time for $R_1(t)$, i.e., a first order parameter such as first order parameter 221, to cross a threshold of 0.95 is even longer for the simulation with added noise (yielding a value of 4.7) as compared to the simulation without noise (yielding a value of 4.5), resulting in improvement factors of 2.1 (with added noise) and 2.0 (with no noise), respectively. Even if average values for the time for $R_1(t)$ to cross the threshold of 0.95 are calculated for values of C±0.1 around the peak value, significantly higher values may be obtained (3.0 for no noise and 2.9 for added noise), resulting in corresponding improvement factors of 1.3 for both situations. Therefore, even if dynamic factor C does not match the optimal value, improvements of more than 25% may be observed independently of added noise.

Influence of the Coupling Strength

The dynamic CR stimulation approach may provide particular advantages in a situation where symptoms are strong (e.g., if a patient is in a state of disease). An intensity of symptoms may, for instance, be measured using established questionnaires (e.g., UPDRS III scores for Parkinson's disease). Since a level of symptom intensity is linked with a level of pathologic connectivity, the dynamic CR stimulation approach should have strong advantages in particular in the first phase of therapy, which is of particular importance for a patient. Therefore, the selected dynamic CR stimulation configuration could be made flexible and dependent on the level or intensity of symptoms. For example, the score level of the used questionnaire could be used as a parameter, e.g., to control dynamic factor C in equations (2)-(6) above. High scores in the questionnaire (e.g., if a patient is in a state of disease) may correspond to values of C deviating significantly from 0 (e.g., C=−0.15), while low scores in the questionnaire (more healthy state of a patient) would correspond to values of C close to 0 (e.g., C=−0.1). As such, the dynamic CR stimulation approach may vary with the course of therapeutic effects, and may further optimize therapeutic results.

Figure 4:
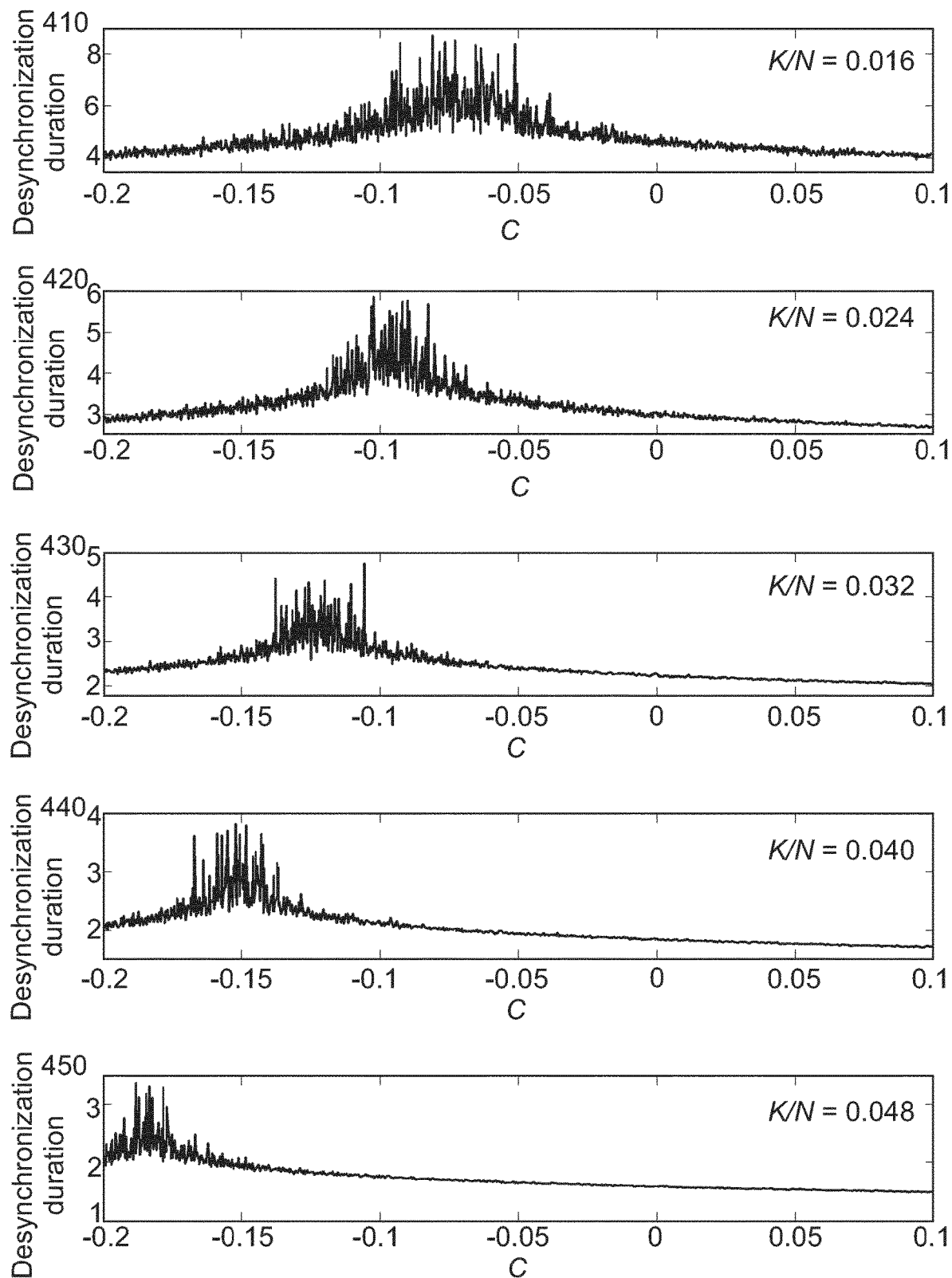
FIG. 4: Desynchronization duration as simulated for different embodiments of the present disclosure.

A level or intensity of symptoms may be understood to be represented in simulations by coupling strength K/N. In FIG. 4 a time for $R_1(t)$, i.e., a first order parameter such as first order parameter 221, to cross a threshold of 0.95 is plotted for different coupling strengths K/N. Dynamic factor C is plotted on the x-axis, while the time for $R_1(t)$ to cross the threshold of 0.95 is plotted on the y-axis. From top panel 410 to bottom panel 450 the coupling strength is increasing from K/N=0.016 to K/N=0.048 as indicated in the upper right corner of each panel 410-450. For lower coupling strengths (cf. panel 410; K/N=0.016, corresponding to a more healthy state of a patient with weaker symptoms) the optimal value of dynamic factor C may be around C=−0.075, while for stronger coupling strengths (cf. panel 450; K/N=0.048, corresponding to a pathologic state of a patient with stronger symptoms) the optimal value of dynamic factor C may be around C=−0.175. For all coupling strengths, the dynamic CR approach is clearly superior to the static CR approach.

By adapting dynamic factor C with respect to the symptom strength or intensity performance of the dynamic CR approach can be further improved.

Number of Stimulation Sites

Superiority of the dynamic CR approach over the static CR approach is given independently of the number of stimulation sites. It is reiterated that stimulation sites may be understood to be synonymous with electrodes. This is important since in clinical practice different numbers of stimulation sites may be available, e.g., if only a part of the stimulation lead, e.g., only some of the total available electrodes or contacts, is located in the target population. The smallest number of stimulation sites required for coordinated reset is two, therefore, numerical tests were performed for two, four, and five stimulation sites and the stimulation onset times given by equation (6) above. For all simulations, the same parameters were used as for the simulations of FIG. 3. Namely, connectivity was kept constant at $$\frac{K}{N} = 0.032,$$

and noise was applied. A length of a stimulation pulses was chosen as 0.2/N to allow longer stimulation pulses for lower numbers of contacts/electrodes and shorter stimulation pulses for higher numbers of contacts/electrodes with the goal to avoid an overlap of stimulation pulses and give space for the adaptation of dynamic factor C.

Figure 5:
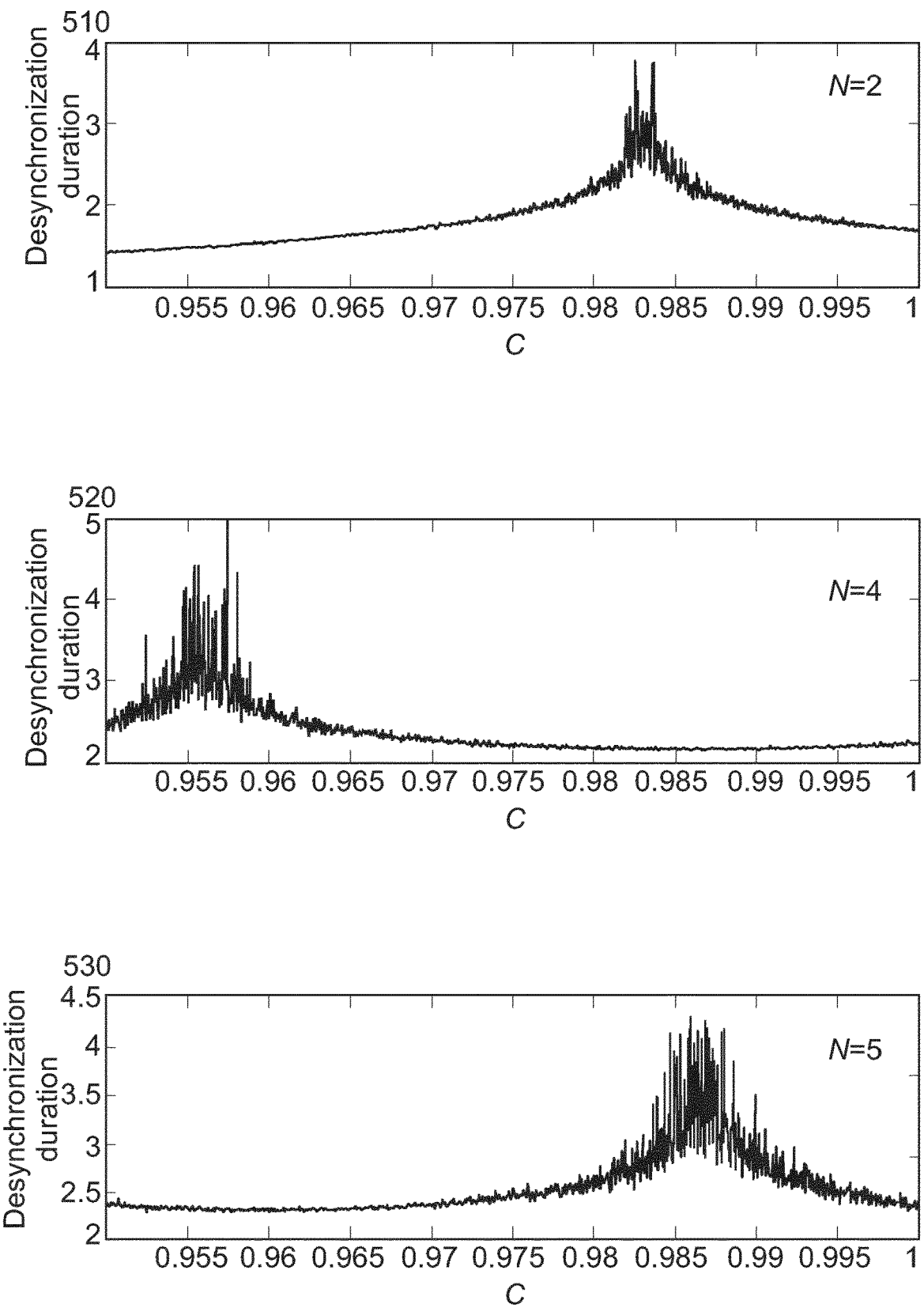
FIG. 5: Desynchronization duration as simulated for different embodiments of the present disclosure.

FIG. 5 shows results of numerical simulations for different numbers of stimulation contacts/electrodes (N=2, 4 and 5, cf. panels 510, 520 and 530, respectively) and different dynamic factors C [0.95, 1.0] plotted on the x-axis. On the y-axis a time until $R_1(t)$, i.e., a first order parameter such as first order parameter 221, crosses a threshold of 0.95 is shown. For all simulations a pronounced and clear peak may be observed for dynamic factors smaller than C=1. Improvement factors of 1.8 (for N=2) to 2.0 (for N=5) may be observed. It is noted that the results for C=1 correspond to the standard static CR approach (cf. equation (6) above) and may be used to evaluate the improvements obtained by the dynamic CR approach with values of C different from 1.

Repetitive Application of Stimulation Cycles

In the above examples, we described the effects of one stimulation cycle 150. But even more effective stimulation and desynchronization may result from application of several of such dynamic CR stimulation cycles. Typical numbers of applied stimulation cycles may be between 1 and 100. For example, 1 or 5 or 10 such stimulation cycles may be applied, followed by either a next sequence of stimulation cycles, or a pause. Typically, the duration of a pause may correspond to the duration of 0 to 100 stimulation cycles, for example to 1 or 5 or 10 cycles.

The order within stimulation cycles, e.g., the particular sequence of pulses within the cycle (such as pulses 130-133 in FIG. 1B) may be chosen to be sequential (i.e., always the same) or random (i.e., changing for each new stimulation cycle). Additionally or alternatively, the device may apply stimulation cycles where a randomly chosen or predefined sequence is used for 1 to 100 consecutive stimulation cycles before a new randomly chosen or predefined embodiment of the stimulation cycles is used.

The effects of dynamic CR stimulation may be realized already with only two stimulation sites (i.e., electrodes). Four stimulation sites may be close to optimal. But stimulation may be applied also through 3, 5 and/or 6 or more stimulation contacts (i.e., electrodes).

All CR stimulation methods, standard and dynamic, are—to some extent—dependent on initial conditions. Only for a certain range of initial conditions, optimal results may be achieved. For a longer sequence of stimulation cycles the effects of different initial conditions may be investigated, since each stimulation cycle comes with new and unpredictable (due to noisy environment) initial conditions. Therefore, longer stimulation sequences may test the robustness of the dynamic CR stimulation approach in a setting which may be close to realistic situations in clinical tests.

Figure 6:
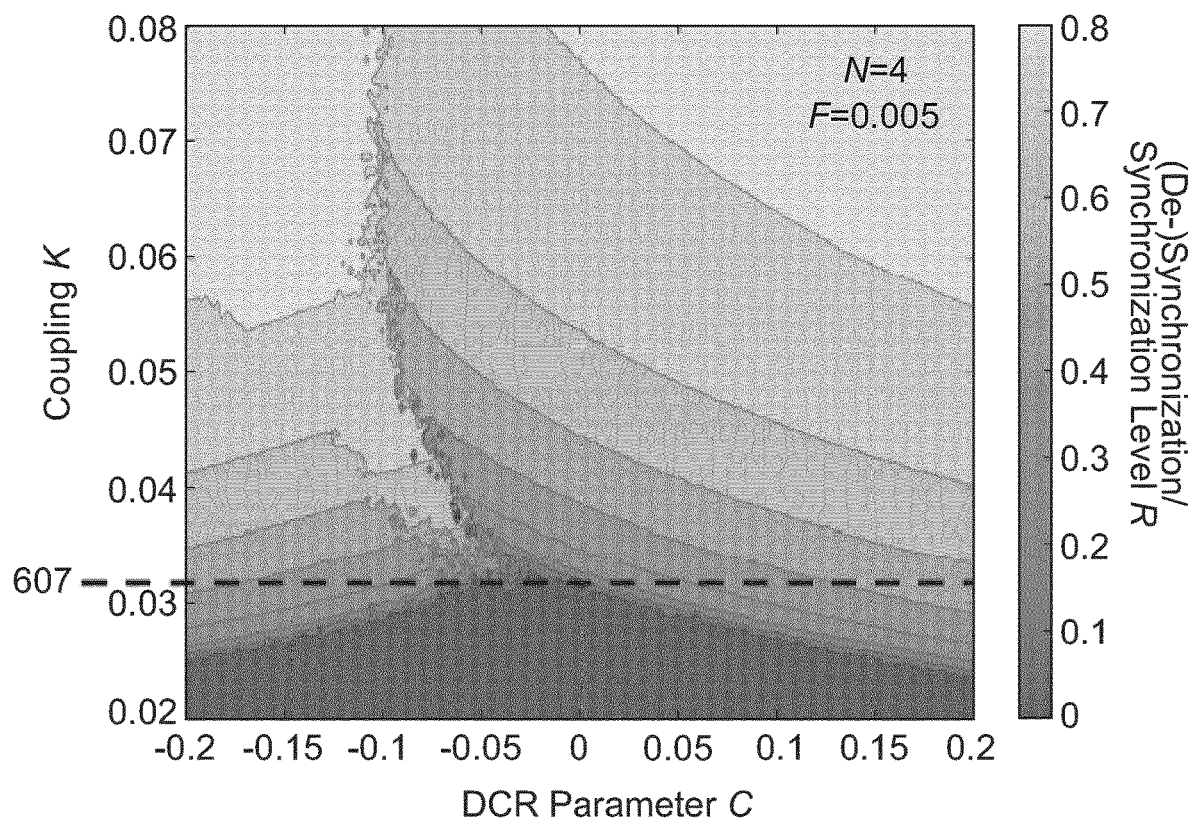
FIG. 6: (De-)synchronization as simulated for different embodiments of the present disclosure.

In simulations underlying FIG. 6 the dynamic CR stimulation described in equation (2) above was tested. Therein, stimulation was applied following a 1 cycle on, 1 cycle off pattern. The simulations were based on N=4, F=0.005. FIG. 6 shows (de-)synchronization as a function of coupling K (plotted on the y-axis) and dynamic factor C (plotted on the x-axis). As can be seen, the value of the dynamic factor C that leads to least synchronization, i.e., to strongest desynchronization, changes with different values for the coupling K. Therefore, it may be desirable to determine the factor C dynamically, hence its name. In particular, it may be desirable to optimize desynchronization with respect to the dynamic factor C, e.g., iteratively.

Figure 7:
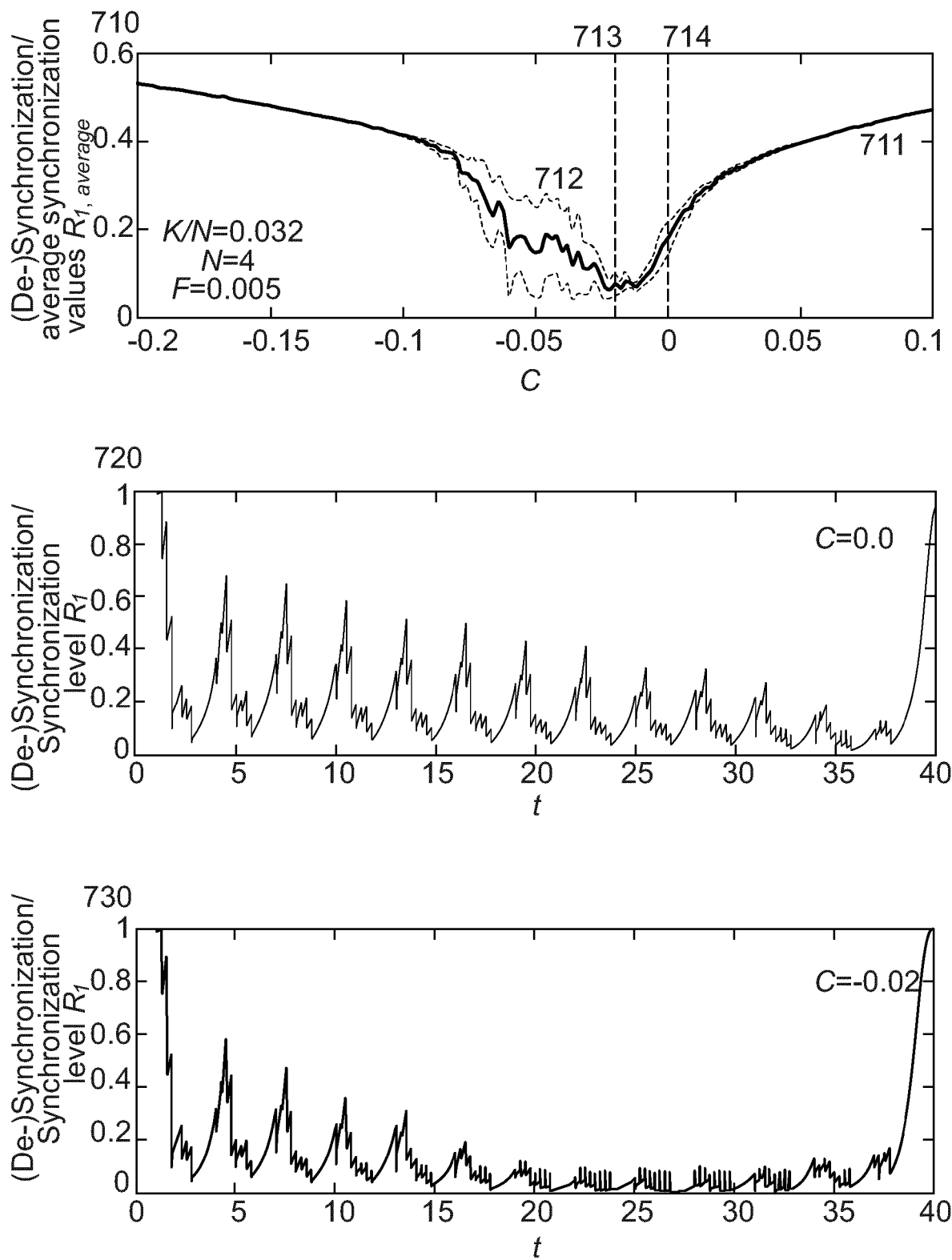
FIG. 7: (De-)synchronization as simulated for different embodiments of the present disclosure.

For a better understanding of the simulation results shown in FIG. 6, reference is made to FIG. 7 which represents a cross-section through FIG. 6 along line 607, representing K/N=0.032. As such, in the simulations underlying FIG. 7, all parameters were effectively chosen as in the simulations underlying FIG. 3, namely, K/N=0.032, N=4, F=0.005. For each value of dynamic factor C plotted on the x-axis of panel 710, ten simulations with different noise realizations but same noise levels were performed and for each simulation a mean value for a synchronization level $R_1$ for $t \in [10,35]$ was calculated (for exemplary results of a single such simulation, see panels 720 and 730 of FIG. 7 which will be discussed below). The solid black line in panel 710 indicates average synchronization values $R_{1,average}$ 711 of these mean synchronization levels $R_1$ calculated for the ten different simulations. The dashed lines in panel 710 indicate a standard deviation 712 to average synchronization values $R_{1,average}$. Best synchronization (corresponding to $R_{1,average}$=0.07 (0.03), the value in brackets specifying the corresponding standard deviation) was observed for values of dynamic factor C in the range of −0.02, indicated by dashed vertical line 713. As can be told from low standard deviation 712 (cf. dashed lines), here the results are very stable. For standard CR stimulation (corresponding to C=0, cf. vertical dashed line 714) the desynchronization effect is worse, indicated by a higher average synchronization value $R_{1,average}$=0.18 (0.04). The improvement in average synchronization value $R_{1,average}$ corresponds to a factor of 2.4.

Panel 720 shows a result of a representative simulation for standard CR stimulation, i.e., C=0. Panel 730 shows a corresponding result of a representative simulation for dynamic CR stimulation with C=−0.02. C=−0.02 corresponds to a forward shift of the onset times of the second and fourth stimulation pulse within the cycle by 2% of the unchanged gap T/N. Similar results may be obtained for stronger coupling K/N.

Demand Controlled Application and Automatic Calibration of Dynamic CR

In some embodiments, dynamic CR stimulation may be combined with a demand-controlled algorithm. Therein, the device may comprise a measurement unit that may identify a need for stimulation. Such a measurement unit may, e.g., record neuronal activity and may identify pathologic neuronal activity, or the measurement unit may detect a tremor, e.g., by using a movement sensor and/or accelerometer. The device may obey an algorithm that starts dynamic CR stimulation only if a demand for stimulation is detected, or the device may control intensity and effectiveness of the dynamic CR stimulation by means of the algorithm. E.g. softer stimulation may be applied if no demand is detected and stronger stimulation may be applied if a demand for stimulation is detected. In some embodiments, the device may also control the dynamic factor C itself based on a calculated level of demand.

Adjustment of dynamic factor C may be done automatically. Invasive application of stimulation contacts (i.e., electrodes) has the advantage that the stimulation contacts may be used as measurement units to detect neuronal activity of a target structure. Thereby, the effect of the stimulation may be measured and analyzed. It is assumed that several stimulation cycles are performed, followed by a stimulation pause with a duration corresponding to several stimulation cycles.

During stimulation pauses the stimulation contacts may be used to detect pathologic neuronal activity. Additionally or alternatively, stimulation may also be performed for a set period of time followed by a longer stimulation break. For example, there may be 3000 cycle periods of stimulation followed by a stimulation break of a duration corresponding to 150 cycle periods. For a cycle period of 200 milliseconds, this results in 10 minutes of stimulation followed by a 30 second stimulation break. In the first place, neuronal activity may for example be measured in a wide range of frequencies, e.g., from 0.1 Hz to 500 Hz. In a second step, for example the frequency range relevant for pathology may be extracted, e.g., a frequency range from 4 to 8 Hz. In a third step, for example, a normalized power within such a frequency range may be calculated, leading to a value between 0 and 1. A low value may correspond to weak to no symptoms, while higher values may correspond to stronger symptoms. These steps may be performed for different values of dynamic factor C.

An additional algorithm may easily detect minima of this curve and may select the corresponding value of dynamic factor C for stimulation.

Such automatic calibration may be performed in short time. For example, if a cycle has a duration of 200 milliseconds, 5 such cycles followed by a pause of a duration corresponding to 5 cycles would take 2 seconds. An interval for dynamic factor C may be scanned by evaluating values of a normalized spectrum of interest for 60 different values of C. Such an automatic calibration may take only 120 seconds. Such an automatic calibration may be either initialized by a health-care professional at each visit in a clinic for readjustment of stimulation parameters and symptom assessment. Or it may be done following a schedule built into an implant comprising a device according to an embodiment of the present disclosure, for example every week, or every day. Since a patient would already benefit from desynchronization and symptom reduction during calibration caused by the stimulation with different values of dynamic factor C (even if not optimized), the patient might not even recognize or be influenced by such an automatic calibration process.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A neurostimulator configured to:
   activate a set of N electrodes, which are each adapted to stimulate at least a portion of a population of neurons when activated and applied in an invasive manner, at respective onset times $T_1 \ldots T_N$ throughout a cycle period T, wherein N is an integer larger than two and wherein the cycle period T is defined as a time period within which each of the N electrodes is activated exactly once, and wherein the onset times $T_1 \ldots T_N$ are not arranged substantially uniformly throughout the cycle period T.

2. The neurostimulator according to claim 1, being further configured to activate the set of N electrodes at the respective onset times $T_1 \ldots T_N$ based at least in part on a state of at least a portion of the population of neurons, wherein the neurostimulator is configured to determine the state based at least in part on determining one or more electrodes that were activated before in the cycle period and/or based at least in part on determining one or more respective onset times at which one or more of the electrodes were activated before in the cycle period and/or based at least in part on a refractory period of at least a portion of the population of neurons.

3. The neurostimulator according to claim 1, wherein the onset times $T_1 \ldots T_N$ at which a respective i-th electrode of the N electrodes is activated in the cycle period T are substantially determined by a function that is nonlinear with respect to i.

4. The neurostimulator according to claim 1, wherein:
   the onset times $T_1 \ldots T_N$ at which a respective i-th electrode of the N electrodes is activated in the cycle period T are substantially given by $T_i = T/N \cdot (i-1) + T/2N \cdot (1+(-1)^i) \cdot C$, wherein $-1 < C < 0$; or
   the onset times $T_1 \ldots T_N$ at which a respective i-th electrode of the N electrodes is activated in the cycle period T are substantially given by $T_i = T/N \cdot (i-1) + T/2N \cdot (1+(-1)^i) \cdot C$, wherein $0 < C < 1$.

5. The neurostimulator according to claim 1, wherein:
   the onset times $T_1 \ldots T_N$ at which a respective i-th electrode of the N electrodes is activated in the cycle period T are substantially given by $T_i = T/N \cdot (i-1) \cdot C$, wherein $0 < C < 1$; or
   the onset times $T_1 \ldots T_N$ at which a respective i-th electrode of the N electrodes is activated in the cycle period T are substantially given by $T_i = 1/N \cdot (i-1) \cdot C$, wherein $1 < C < N/N-1$.

6. The neurostimulator according to claim 1, wherein:
   the onset times $T_1 \ldots T_N$ at which a respective i-th electrode of the N electrodes is activated in the cycle period T are substantially given by $T_i = T/N \cdot (i-1) + T \cdot C$, wherein $C=0$ for $i=1$ and $-1/N < C < 0$ for $i>1$; or
   the onset times $T_1 \ldots T_N$ at which a respective i-th electrode of the N electrodes is activated in the cycle period are substantially given by $T_i = T/N \cdot (i-1) + T \cdot C$, wherein $0 < C < 1/N$.

7. The neurostimulator according to claim 1, wherein:
   the onset times $T_1 \ldots T_N$ at which a respective i-th electrode of the N electrodes is activated in the cycle period T are substantially given by $T_i = T/N \cdot (i-1) + T \cdot (N+1-i) \cdot C$, wherein $C=0$ for $i=1$ and $-1/N \cdot (N-1) < C < 0$ for $i>1$; or
   the onset times $T_1 \ldots T_N$ at which a respective i-th electrode of the N electrodes is activated in the cycle period T (150) are substantially given by $T_i = T/N \cdot (i-1) + T \cdot (N+1-i) \cdot C$, wherein $0 < C < 1/N$.

8. The neurostimulator according to claim 1, wherein:

the onset times $T_1 \ldots T_N$ at which a respective i-th electrode of the N electrodes is activated in the cycle period T are substantially given by $T_1 = 0$ for i=1 and by $T_i = T_{i-1} + T/N \cdot C^{N+1-i}$ for i>1, wherein $0 < C < 1$; or the onset times $T_1 \ldots T_N$ at which a respective i-th electrode of the N electrodes is activated in the cycle period T are substantially given by $T_1 = 0$ for i=1 and by $T_i = T_{i-1} + T/N \cdot C^{N+1-i}$ for i>1, wherein $1 < C$ and $C^N - C/C - 1 < N$.

9. The neurostimulator according to claim 1, being configured such that, at the respective onset time, the N electrodes are respectively activated for a respective activation time each and the activation times overlap in time not at all or only in part.

10. The neurostimulator according to claim 1, being further configured to activate the set of N electrodes throughout at least two and at most one hundred consecutive cycle periods.

11. The neurostimulator according to claim 1, being further configured to activate a further set of M electrodes different from the set of N electrodes throughout at least two and at most one hundred cycle periods based at least in part on a state of the population of neurons, wherein M is an integer.

12. The neurostimulator according to claim 1, being further configured to not activate any of the electrodes for a duration corresponding to at least one cycle period and at most one hundred cycle periods in alternation with activating the electrodes throughout at least one and at most one hundred consecutive cycle periods.

13. The neurostimulator according to claim 4, being further configured to determine C based at least in part on an intensity of symptoms resulting from synchronized neuronal brain activity.

14. The neurostimulator according to claim 13, being further configured to determine C by carrying out stimulations using values of C that lie around an initial value of C determined based at least in part on the intensity of the symptoms.

15. The neurostimulator according to claim 1, wherein the neurostimulator comprises stimulation leads connected to the electrodes and one or more computer processors configured by computer program code to perform the step of activating the set of N electrodes via the stimulation leads.

16. The neurostimulator according to claim 15, further comprising the electrodes which are applied in the invasive manner in a brain.

17. The neurostimulator according to claim 15, wherein the one or more computer processors are associated with a pulse generator which is configured to generate pulses for activating the set of N electrodes via the stimulation leads such that the onset times $T_1 \ldots T_N$ are not arranged substantially uniformly throughout the cycle period T.

18. A method for neurostimulation comprising:

activating a set of N electrodes, which are each adapted to stimulate at least a portion of a population of neurons when activated and applied in an invasive manner, at respective onset times $T_1 \ldots T_N$ throughout a cycle period T, wherein N is an integer larger than two and wherein the cycle period T is defined as a time period within which each of the N electrodes is activated exactly once, and wherein the onset times $T_1 \ldots T_N$ are not arranged substantially uniformly throughout the cycle period T.

19. The method according to claim 18, wherein the method is performed with the electrodes applied in the invasive manner in a brain for desynchronizing neuronal brain activity.

20. A tangible, non-transitory computer-readable medium comprising instructions, which upon being executed by one or more computer processors of a neurostimulator, cause execution of the following steps:

activating a set of N electrodes, which are each adapted to stimulate at least a portion of a population of neurons when activated and applied in an invasive manner, at respective onset times $T_1 \ldots T_N$ throughout a cycle period T, wherein N is an integer larger than two and wherein the cycle period T is defined as a time period within which each of the N electrodes is activated exactly once, and wherein the onset times $T_1 \ldots T_N$ are not arranged substantially uniformly throughout the cycle period T.

* * * * *